(12) United States Patent
Cheng et al.

(10) Patent No.: US 11,747,246 B2
(45) Date of Patent: Sep. 5, 2023

(54) COAL ROCK THREE-DIMENSIONAL STRAIN FIELD VISUAL SYSTEM AND METHOD UNDER COMPLEX GEOLOGICAL STRUCTURE

(71) Applicants: North China Institute Of Science And Technology, Beijing (CN); Chongqing University, Chongqing (CN)

(72) Inventors: Zhiheng Cheng, Beijing (CN); Haobin Gao, Zhaoyuan (CN); Quanle Zou, Zhenping County (CN); Liang Chen, Beijing (CN); Jiakai Sun, Beijing (CN); Bichuan Zhang, Chongqing (CN); Fanjie Kong, Taiyuan (CN); Biao Liu, Xiangtan County (CN); Ruizhi Wang, Chengdu (CN)

(73) Assignees: NORTH CHINA INSTITUTE OF SCIENCE AND TECHNOLOGY, Beijing (CN); CHONGQING UNIVERSITY, Chongqing (CN)

( * ) Notice: Subject to any disclaimer, the term of this patent is extended or adjusted under 35 U.S.C. 154(b) by 203 days.

(21) Appl. No.: 17/349,262

(22) Filed: Jun. 16, 2021

(65) Prior Publication Data
US 2021/0389219 A1    Dec. 16, 2021

(30) Foreign Application Priority Data
Jun. 16, 2020  (CN) .......................... 202010546108.6

(51) Int. Cl.
*G01N 3/00* (2006.01)
*G01N 3/06* (2006.01)
(Continued)

(52) U.S. Cl.
CPC ........... *G01N 3/068* (2013.01); *G01N 1/2806* (2013.01); *G01N 3/08* (2013.01); *B33Y 10/00* (2014.12);
(Continued)

(58) Field of Classification Search
CPC .......... G01L 5/0028; G01L 1/22; A61M 5/24; G01N 3/068; G01N 1/2806; G01N 3/08;
(Continued)

(56) References Cited

U.S. PATENT DOCUMENTS

2014/0208683 A1* 7/2014 Soucy ..................... E02D 17/20
                                                    52/741.15
2020/0018671 A1* 1/2020 Zhang .................... H04N 23/54
(Continued)

FOREIGN PATENT DOCUMENTS

CN          207488084 U  *  6/2018    ............... G01N 3/12

*Primary Examiner* — Max H Noori
(74) *Attorney, Agent, or Firm* — WPAT, PC

(57) ABSTRACT

Coal rock three-dimensional strain field visual system and method are provided under a complex geological structure. The system includes a stress condition simulation system and a strain monitoring system. The stress condition simulation system includes a similar simulation experiment rack, a loading system and a circular slideway. The method includes preparing a 3D printing wire, printing a strain visual similar model, simulating a stratum dip angle and a gas-containing condition, applying stress fields, recording a cracking and dyeing condition of microcapsules inside the model, and the like. The system can realize tracing the generation and development of internal cracks in simulation models with complex geological conditions, and tracing the three-dimensional movement of internal ink dots to draw four-dimensional images of displacement fields.

4 Claims, 3 Drawing Sheets

(51) Int. Cl.
  *G01N 1/28* (2006.01)
  *G01N 3/08* (2006.01)
  *B33Y 10/00* (2015.01)
  *B33Y 80/00* (2015.01)

(52) U.S. Cl.
  CPC ...... *B33Y 80/00* (2014.12); *G01N 2203/0019* (2013.01); *G01N 2203/0066* (2013.01); *G01N 2203/0254* (2013.01); *G01N 2203/0652* (2013.01)

(58) Field of Classification Search
  CPC ... G01N 2203/0019; G01N 2203/0066; G01N 2203/0254; G01N 2203/0652; B33Y 10/00; B33Y 80/00
  See application file for complete search history.

(56) References Cited

U.S. PATENT DOCUMENTS

2020/0319070 A1* 10/2020 Liu ........................... G01N 3/12
2022/0178802 A1* 6/2022 Guo ........................... G01N 3/08
2022/0349147 A1* 11/2022 Li ............................. E21F 17/00

* cited by examiner

COAL ROCK THREE-DIMENSIONAL STRAIN FIELD VISUAL SYSTEM AND METHOD UNDER COMPLEX GEOLOGICAL STRUCTURE

TECHNICAL FIELD OF THE INVENTION

The invention relates to the field of machinery and mine technology engineering, in particular to a coal rock three-dimensional strain field visual system and method under a complex geological structure.

BACKGROUND OF THE INVENTION

As an important research method of a stratum control technology, similar simulation experiment has been widely accepted and recognized. However, in the traditional similar simulation experiment, it is impossible to observe the internal strain field distribution of the materials visually rather than an indirect measuring method, thereby causing greater errors, destroying the integrity of the model and generating unnecessary errors. By constructing the model from a transparent microcapsule composite material, the strain field distribution inside the model can be visually observed in real time without destroying the integrity of the model. At present, the 3D printing technology has been widely used to construct the model; by improving the shortcomings that the conventional model manufacturing method has difficulty in avoiding applying stress to the material and easily damages the internal microcapsules of the composite material, the 3D printing technology has advantages of being quick in forming, precise, free of prestress, and the like, and has a wide application prospect in similar simulation tests.

Therefore, it is urgent to develop a coal rock strain visual system under a complex geological structure.

SUMMARY OF THE INVENTION

The objective of the invention is to provide a coal rock three-dimensional strain field visual system and method under a complex geological structure to solve the problems existing in the prior art.

The technical solution adopted to achieve the objective of the invention is as follows: a coal rock three-dimensional strain field visual system under a complex geological structure includes a stress condition simulation system and a strain monitoring system.

The stress condition simulation system includes a similar simulation experiment rack, a loading system and a circular slideway.

The similar simulation experiment rack includes a pressure chamber and two visual side plates. The pressure chamber is a rectangular frame body as a whole. The two open ends of the rectangular frame body can be sealed by the visual side plates. The pressure chamber and the visual side plates are enclosed to define a model placing cavity.

The loading system includes a vertical axial pressure loading system and a horizontal stress loading system. The vertical axial pressure loading system loads set vertical loading force to the top and the bottom of the pressure chamber. The horizontal stress loading system loads set horizontal loading force to the left side of the pressure chamber.

The strain monitoring system includes a plurality of multi-angle high-speed cameras.

In work, the vertical axial loading system applies an uneven force on the model to simulate the time-varying law of the three-dimensional strain fields inside the coal and rock mass under the complex geological structure.

The invention further discloses a coal rock three-dimensional strain field visual method under a complex geological structure adopting the system according to claim 1, including the following steps:

1) heating and melting a transparent base material to uniformly mix with the ink microcapsules to prepare a 3D printing wire;

2) performing geological structure 3D printing in the model placing cavity of the stress condition simulation system to obtain a strain visual similar model;

3) utilizing the stress condition simulation system to simulate a stratum dip angle, a geological structure and a gas-containing situation;

4) after the model is cooled, applying three-dimensional stress on the model, where the ink microcapsules were broken under the stress to dye the surrounding materials and cracks;

5) utilizing a multi-angle high-speed camera to record the cracking and dyeing condition of microcapsules inside the model; and 6) tracing the displacement of the ink dots after the microcapsules are cracked, and reconstructing the four-dimensional strain fields in the monitoring model.

Furthermore, the capsule walls of the ink microcapsules are made of a polyurethane material, and the capsule cores are made of dying ink. The transparent base material is silicone resin.

Furthermore, in the step 2), mica powder is used to separate the layers of similar model rock layers.

Furthermore, in the step 3), the loading system applies different forces to the model to simulate a complex geological structure condition under which coal rock is located, and after the model is fixed on the experiment rack, the experiment rack can be rotated through the circular slideway to adjust the angle to simulate the stratum dip angle.

The technical effects of the invention are beyond doubt:

A, the generation and development of internal cracks in simulation models with similar geological conditions can be traced, and the three-dimensional movement of internal ink dots can be traced to draw four-dimensional images of displacement fields;

B, Strain visualization makes the division of the stress action range clearer, and the action effect more significant. Compared with the traditional model, the strain visual model more clearly reflects the action effect of the force in the model, and avoids destroying the completeness of the model for arranging the stress sensor;

C, the 3D printing construction model avoids excessive cracking of the microcapsules during the modeling process;

D, the multi-angle high-speed camera unit solves the defects that a single camera cannot form stereo vision and cannot draw three-dimensional images;

E, the system can be used to trace the formation and development of cracks under stress; and F, the system can be used to analyze the four-dimensional distribution of the displacement fields in the model under stress.

Figure 1:
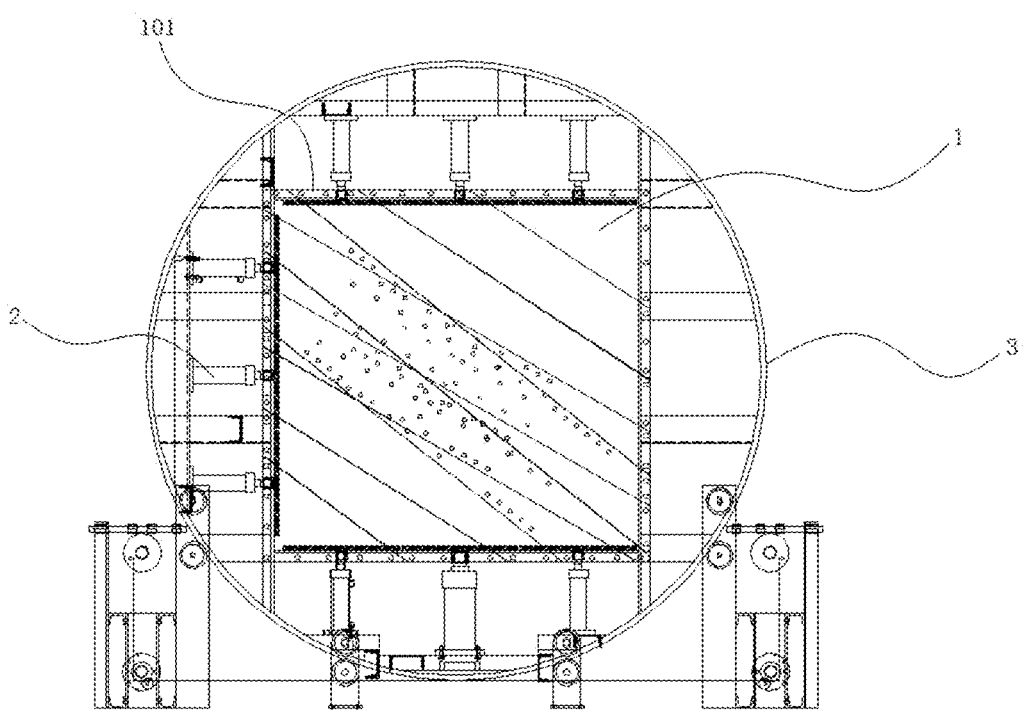
FIG. 1 is a schematic diagram showing the structure of a stress condition simulation system.
Figure 2:
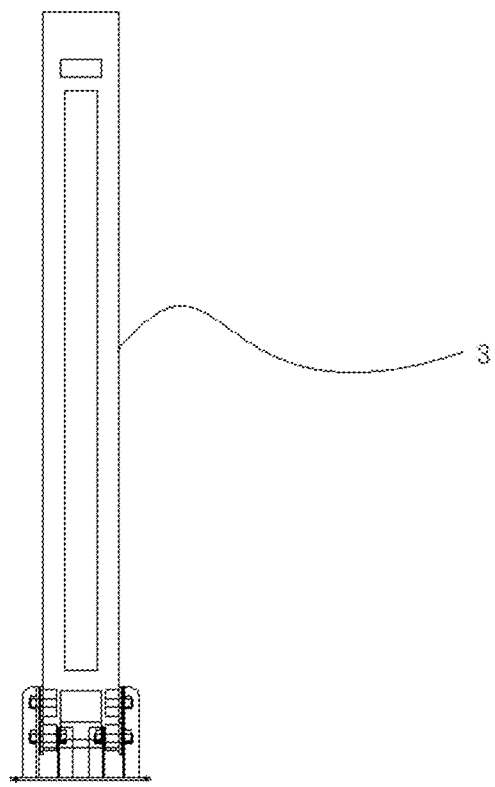
FIG. 2 is a side view of the stress condition simulation system.
Figure 3:
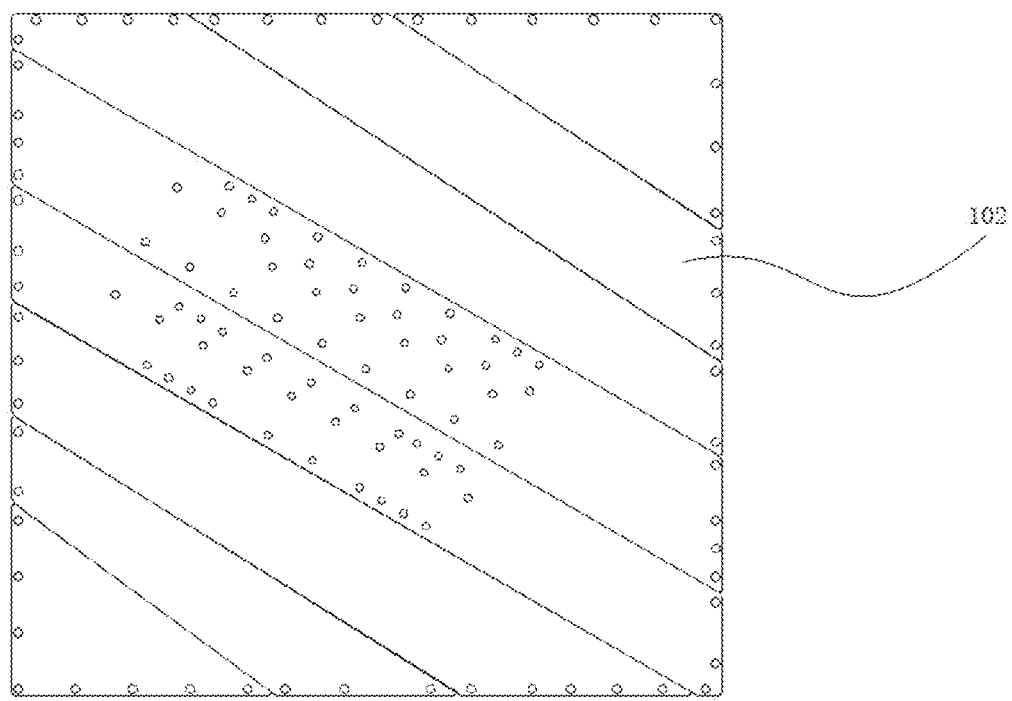
FIG. 3 is a schematic diagram showing the structure of a visual side plate.

In the figures: similar simulation experiment frame 1, pressure chamber 101, visual side plate 102, loading system 2 and circular slideway 3.

DETAILED DESCRIPTION OF THE PREFERRED EMBODIMENTS

The invention will be further described below in conjunction with embodiments, but it should not be understood that the scope of the above subject matter of the present invention is limited to the following embodiments. Without departing from the above technical idea of the invention, various substitutions and changes based on common technical knowledge and conventional means in the field should be included in the protection scope of the invention.

Embodiment 1

Refer to FIG. 1 to FIG. 4, the embodiment of the invention discloses a coal rock three-dimensional strain field visual system under a complex geological structure, including a stress condition simulation system and a strain monitoring system.

The stress condition simulation system includes a similar simulation experiment rack 1, a loading system 2 and a circular slideway 3.

The similar simulation experiment rack 1 includes a pressure chamber 101 and two visual side plates 102. The pressure chamber 101 is a rectangular frame body as a whole. The two open ends of the rectangular frame body can be sealed by the visual side plates 102. The pressure chamber 101 and the visual side plates 102 are enclosed to define a model placing cavity.

The loading system 2 includes a vertical axial pressure loading system and a horizontal stress loading system. The vertical axial pressure loading system loads set vertical loading force to the top and the bottom of the pressure chamber 101. The horizontal stress loading system loads set horizontal loading force to the left side of the pressure chamber 101.

The strain monitoring system includes a plurality of multi-angle high-speed cameras.

In work, the vertical axial loading system applies an uneven force on the model to simulate the time-varying law of the three-dimensional strain fields inside the coal and rock mass under the complex geological structure; and after the model is fixed on the experiment rack, the experiment rack can be rotated by the circular slideway to adjust the angle to simulate a stratum dip angle.

Embodiment 2

Figure 4:
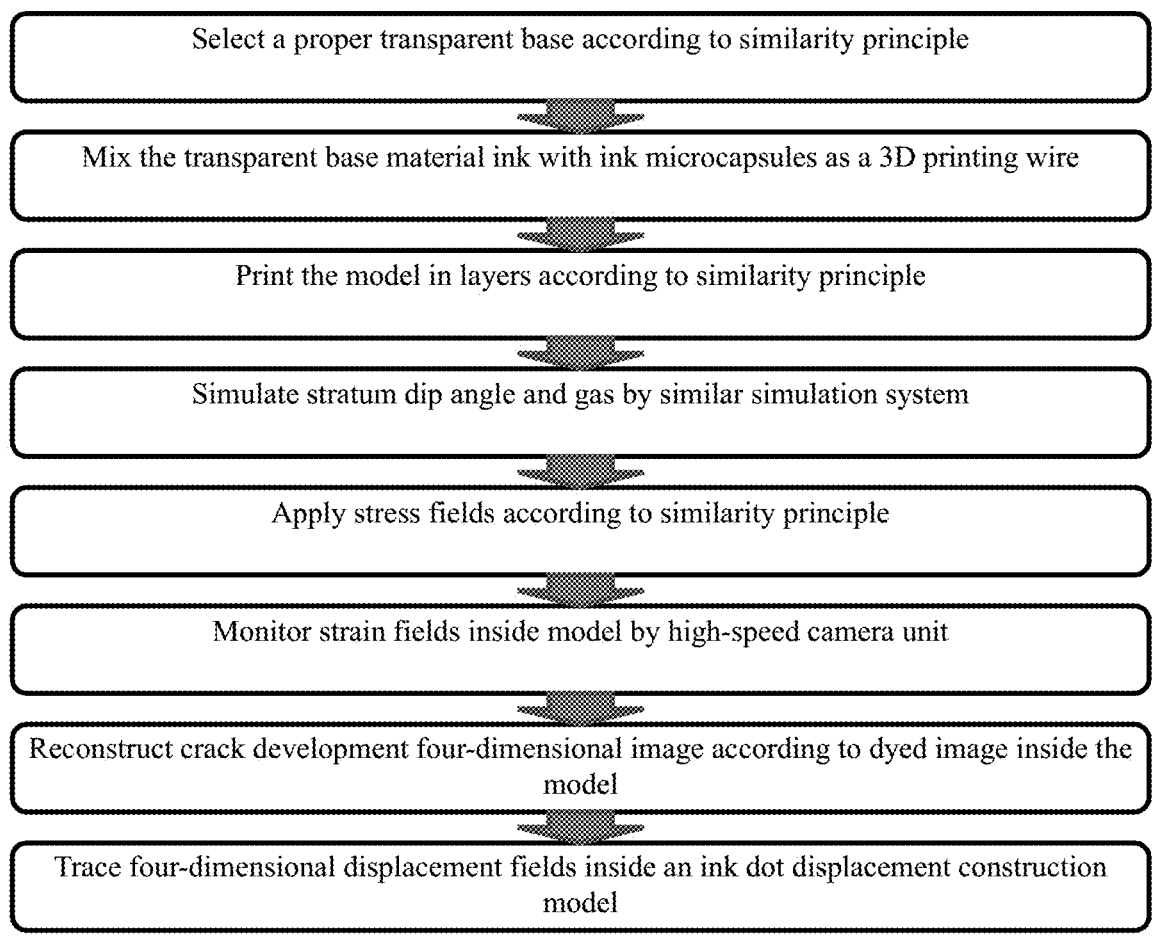
FIG. 4 is a flowchart of a method.

Refer to FIG. 4, the embodiment of the invention disclosed a coal rock three-dimensional strain field visual method under a complex geological structure adopting the system of the Embodiment 1, including the following steps that:

1) a transparent base material was heated and melted to uniformly mix with the ink microcapsules to prepare a 3D printing wire, where capsule walls of the ink microcapsules were made of a polyurethane material, and the capsule cores were made of dying ink; the transparent base material was silicone resin;

in this embodiment, the ink microcapsules were synthesized by a chemical method; the chemical method, also known as an in-situ polymerization method, referred to a series of reaction conditions such as adjusting the temperature of a reaction system, adjusting the pH value or adding electrolytes, catalysts, etc., so that small monomer molecules were polymerized to form polymer film-forming materials and precipitated from the solution to cover the core material; in the entire reaction system, the core material was dispersed into fine particles through mechanical stirring and emulsification, and the polymerization reaction proceeded on the surfaces of the core material droplets; at the beginning of the reaction, monomers X and Y were first pre-polymerized; as the thermal curing crosslinking reaction proceeded, —(X—Y)-n was the polymer capsule wall finally formed, and finally, the core material and the wall material were polymerized to form microcapsules; the microcapsules prepared by this method had a high film-forming rate and relatively stable properties;

It should be noted that the thickness of the capsule walls should be moderate, which can not only withstand the pressure brought by the molding process of the matrix material, but also feel the force brought by the crack extension; and the hardness of the capsules that can be broken in time under the stress cannot be too great, so that cracks can pass through rather than get across. the inner cores of the microcapsules had a suitable dyeing effect which could be observed by slight crushing, and the more crushing, the deeper the dyeing; and the melting points of the capsule walls were higher than the melting point of the base material to prevent the microcapsule walls from dissolving and leaking out during the mixing process and printing process.

2) geological structure 3D printing was performed in the model placing cavity of the stress condition simulation system to obtain a strain visual similar model; mica powder was used to separate the layers of similar model rock layers.

3) the stress condition simulation system was utilized to simulate a stratum dip angle, a geological structure and a gas-containing situation, and the experiment rack was rotated by the circular slideway to adjust the angle to simulate the stratum dip angle after the model was fixed onto the experiment rack, 4) after the model was cooled, uneven stress fields are applied to the top of the model to simulate the effect of gravity on the coal and rock mass with a simple geological structure. where the ink microcapsules were broken under the stress to dye the surrounding materials and cracks;

5) a multi-angle high-speed camera was utilized to record the cracking and dyeing condition of microcapsules inside the model, the crack fields of the material could also be restored by tracing and monitoring cracked dyed points; the evolution of cracks can be obtained by using high-speed cameras to observe similar models as the stress increased and the process of crack initiation and expansion was combined with fractal theory to obtain the evolution law of mining cracks; the evolution law of mining cracks included the evolution of the number, opening degree, area, type and fractal dimension of mining cracks as the mining proceeded; the position of the ink dot was traced after cracking, and plus the time axis, could draw a four-dimensional displacement field distribution image in the model;

multiple multi-angle high-speed camera units were utilized to trace the expansion of the microcapsule dyed area, so that the spread of the instantaneous crack fields in the three-dimensional space could be obtained; the three-dimensional stress freezing technology was used to extract the stress fields at different slices and then combine the stress changes in different excavation processes to perform four-dimensional reconstruction to obtain the four-dimensional strain distribution in the model; and the position changes of the ink dot were traced after cracking to obtain four-dimensional displacement field distribution in the model;

6) the displacement of the ink dots was traced after the microcapsules were cracked, and the four-dimensional strain fields were reconstructed in the monitoring model;

by combining the microcapsule composite material, the 3D printing technology, the similar simulation system and the multi-angle high-speed camera unit in this embodiment, the generation and development of internal cracks in simulation models with similar geological conditions could be traced, and the three-dimensional movement of internal ink dots could be traced to draw four-dimensional images of displacement fields.

It should be noted that under the action of the static stress fields, the microcapsule cracked dyed area was the distribution area of the stress fields greater than the microcapsule crack threshold; the denser the microcapsule cracks, the deeper the dyeing and the greater the stress.

Embodiment 3

The main steps of this embodiment were the same as those of embodiment 2. In step 4), relatively large stress was applied to the left side of the top of the coal seam, and relatively large stress was applied to the right side of the bottom of the coal seam. The model had faults under the action of shear stress, and simulated the situation near the geological structure of coal and rock mass faults.

Embodiment 4

The main steps of this embodiment were the same as those of embodiment 2. In step 4), relatively large stress was applied to the left side and the right side of the top of the coal seam, relatively small stress was applied to the middle, relatively small stress was applied to left and right sides of the bottom, relatively large stress was applied to the middle, and certain stress was applied to the side surface, so that the model folded and simulated the situation near the folded geological structure of the coal and rock mass.

What is claimed is:

1. A coal rock three-dimensional strain field visual method under a complex geological structure adopting a coal rock three-dimensional strain field visual system, comprising the following steps:
   1) heating and melting a transparent base material to uniformly mix with ink microcapsules to prepare a 3D printing wire;
   2) performing geological structure 3D printing in a model placing cavity of a stress condition simulation system to obtain a strain visual similar model;
   3) utilizing the stress condition simulation system to simulate a stratum dip angle, a geological structure and a gas-containing situation;
   4) after the model is cooled, applying a three-dimensional stress to the model, wherein the ink microcapsules are broken under the stress to dye surrounding materials and cracks;
   5) utilizing a multi-angle high-speed camera to record a cracking and dyeing condition of the ink microcapsules inside the model; and
   6) tracing a displacement of ink dots after the ink microcapsules are cracked, and reconstructing four-dimensional strain fields in the model;

wherein the coal rock three-dimensional strain field visual system, comprises: the stress condition simulation system and a strain monitoring system, the stress condition simulation system comprises a similar simulation experiment rack, a loading system and a circular slideway;

the similar simulation experiment rack comprises a pressure chamber and two visual side plates; the pressure chamber is a rectangular frame body as a whole; two open ends of the rectangular frame body are sealed by the visual side plates; the pressure chamber and the visual side plates are enclosed to define the model placing cavity;

the loading system comprises a vertical axial pressure loading system and a horizontal stress loading system, the vertical axial pressure loading system loads set vertical loading force to a top and a bottom of the pressure chamber; the horizontal stress loading system loads set horizontal loading force to a left side of the pressure chamber;

the strain monitoring system comprises a plurality of multi-angle high-speed cameras;

and in work, the vertical axial loading system applies an uneven force on the model to simulate a time-varying law of three-dimensional strain fields inside coal and rock mass under the complex geological structure.

2. The coal rock three-dimensional strain field visual method under the complex geological structure according to claim 1, wherein capsule walls of the ink microcapsules are made of a polyurethane material, and capsule cores are made of dying ink; and the transparent base material is silicone resin.

3. The coal rock three-dimensional strain field visual method under the complex geological structure according to claim 1, wherein in the step 2), mica powder is used to separate layers of similar model rock layers.

4. The coal rock three-dimensional strain field visual method under the complex geological structure according to claim 1, wherein in the step 3), the loading system applies different forces to the model to simulate a complex geological structure condition under which coal rock is located.

\* \* \* \* \*